| United States Patent [19] | [11] Patent Number: 4,985,039 |
|---|---|
| Endlweber | [45] Date of Patent: Jan. 15, 1991 |

[54] PRESERVING ANIMAL HIDES

[75] Inventor: Hans Endlweber, Vienna, Austria

[73] Assignee: Messer Griesheim GmbH, Fed. Rep. of Germany

[21] Appl. No.: 385,190

[22] Filed: Jul. 26, 1989

[30] Foreign Application Priority Data

Aug. 12, 1988 [DE] Fed. Rep. of Germany ....... 3827382

[51] Int. Cl.$^5$ ............................................... C14C 1/00
[52] U.S. Cl. ................................... 8/94.15; 8/94.1 R; 62/384
[58] Field of Search .......................... 8/94.1 R, 94.15; 62/384

[56] References Cited

U.S. PATENT DOCUMENTS

| 31,640 | 5/1861 | Wyeth | 8/94.15 |
| 4,166,364 | 9/1979 | Ruprecht et al. | 62/384 |
| 4,206,616 | 6/1980 | Frank et al. | 62/384 |

Primary Examiner—Paul Lieberman
Assistant Examiner—John F. McNally
Attorney, Agent, or Firm—Connolly & Hutz

[57] ABSTRACT

In order to have a preservation process that is environmentally safe and that prevents bacterial or enzymatic decomposition of the hides, the hides are treated with $CO_2$ immediately after being pulled off.

6 Claims, No Drawings

PRESERVING ANIMAL HIDES

BACKGROUND OF INVENTION

The "raw" hide that is removed from animals is only rarely processed immediately in a leather factory. Collecting and sorting the hides according to weight classes, compiling the "batches" and transporting the hides to the leather factory take at least a few days, often weeks or even months. Due to its protein content, untanned hide in its natural, wet state is a breeding ground for bacteria. In order to protect it from damage due to rotting, it must be preserved.

In order to prevent putrefactive bacteria from decomposing the hide substance, the simplest measure is to adequately reduce the water content in the hide. In tropical countries, the hides are air-dried. This requires a great deal of space and can only be carried out with small numbers of hides.

Usually, common salt is used for preservation; blood and dung are cleaned off the hides and they are either sprinkled with grains of salt or soaked for approximately 24 hours in a saturated saline solution. After the salt treatment, they are stacked on a slanted base so that the surplus brine can drain off; the hides are then bundled together. The water content of the hides drops from about 65% to about 40% as a result of the salt preservation step.

When the preserved hides are processed in the leather factory, the preservation salt is washed off with the waste water, which causes considerable water pollution.

For this reason, preservation has already been tried with an aqueous solution of sodium sulfide and acetic acid. However, the antimicrobial effect was not satisfactory.

SUMMARY OF INVENTION

The object of the invention is to create a preservation process that is environmentally safe and that prevents bacterial and enzymatic decomposition of the hides.

According to the invention, the proposal is made to treat the hides with $CO_2$ immediately after they have been pulled off or skinned from the body of the animal. It is especially advantageous if this is done in such a manner that the hides are immediately shock-cooled after being pulled off, and then stored in a $CO_2$ atmosphere.

DETAILED DESCRIPTION

The shock-cooling procedure is preferably carried out with $CO_2$ snow (i.e. $CO_2$ in its solid state) having a temperature of approx. $-79°$ C. ($-110.2°$ F.). As the temperature rises, the $CO_2$ evaporates and it can be used entirely or partially as storage gas.

One storage possibility is to place the hides, sorted by weight, in containers and preferably to sprinkle each hide with $CO_2$ snow. After the container is filled, it is then closed. In order to prevent excess pressure from building up, the container must have a safety device.

In smaller slaughter houses, the hides are usually placed in containers without being sorted and these containers are then filled with $CO_2$ gas.

In both cases, it is advantageous to admit $CO_2$ into the container until the $O_2$ content is less than 1%. This means long-lasting storage stability.

The container should preferably be made of plastic with internal dimensions of approx. 1 to 1.5 m$^3$. If the containers are kept in cold storage, the temperature in the container can be kept low for a long time.

What is claimed is:

1. Process to conserve hides, characterized by the following steps:
    (a) cleaning the hides after they have been skinned from the body of the animal in order to remove meat, blood, fat and other impurities;
    (b) contacting the cleaned hides with $CO_2$ at a temperature of about $-79°$ C. to provide a temperature which brings about a very rapid, shock freezing of the hides; and
    (c) storing the frozen hides in a $CO_2$ atmosphere.

2. Process according to one of the claims 1 characterized in that the hides are stored in plastic containers.

3. Process according to claim 1, characterized in that the contacting step is performed with the $CO_2$ at a temperature of about $-79°$ C., the storage step being done by placing the hides in a container and, after the container is closed, the atmosphere in it is displaced by $CO_2$ until the $O_2$ content is less than 1%.

4. Process according to claim 1, characterized by the use of $CO_2$ snow as the coolant.

5. Process according to claim 1, characterized by a $CO_2$-storage atmosphere with an $O_2$ content of less than 1%.

6. Process according to claim 1, characterized by the contacting step being performed with the $CO_2$ at a temperature of about $-79°$ C.

* * * * *